United States Patent

Kurihara (10) Patent No.: US 9,943,957 B2
(45) Date of Patent: Apr. 17, 2018

(54) METHOD FOR CONTROLLING MEDICAL MANIPULATOR

(71) Applicant: OLYMPUS CORPORATION, Tokyo (JP)

(72) Inventor: Kyohei Kurihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/375,388

(22) Filed: Dec. 12, 2016

(65) Prior Publication Data

US 2017/0087714 A1 Mar. 30, 2017

Related U.S. Application Data

(63) Continuation of application No. PCT/JP2015/065943, filed on Jun. 2, 2015.

(30) Foreign Application Priority Data

Jun. 20, 2014 (JP) ................................ 2014-127253

(51) Int. Cl.
| | |
|---|---|
| G05B 15/00 | (2006.01) |
| B25J 3/00 | (2006.01) |
| A61B 90/00 | (2016.01) |
| A61B 34/32 | (2016.01) |
| A61B 34/37 | (2016.01) |
| A61B 34/00 | (2016.01) |
| A61B 1/00 | (2006.01) |

(Continued)

(52) U.S. Cl.
CPC ............. *B25J 3/00* (2013.01); *A61B 1/00133* (2013.01); *A61B 1/018* (2013.01); *A61B 34/32* (2016.02); *A61B 34/37* (2016.02); *A61B 34/71* (2016.02); *A61B 90/00* (2016.02); *A61B 1/00039* (2013.01)

(58) Field of Classification Search
None
See application file for complete search history.

(56) References Cited

U.S. PATENT DOCUMENTS

| 5,064,353 A | 11/1991 | Tsukahara |
| 2009/0143642 A1 | 6/2009 | Takahashi et al. |

FOREIGN PATENT DOCUMENTS

| JP | S57-160381 A | 10/1982 |
| JP | H01-231676 A | 9/1989 |

(Continued)

OTHER PUBLICATIONS

International Search Report dated Sep. 29, 2015 issued in PCT/JP2015/065943.

(Continued)

*Primary Examiner* — Bhavesh V Amin
(74) *Attorney, Agent, or Firm* — Scully, Scott, Murphy & Presser, P.C.

(57) ABSTRACT

The method for controlling a medical manipulator is a method for controlling a medical manipulator which drives a driven part by rotating a motor in accordance with an operation input from an operation part. The method includes: a first step of performing a trial driving when the operation input occurs, and evaluating changes in winding resistance based on a temperature rise of the motor, and setting a driving condition of the motor based on the evaluated changes winding resistance; and a second step of performing driving which corresponds to the operation input based on the driving condition of the motor set in the first step.

4 Claims, 6 Drawing Sheets

(51) Int. Cl.
    *A61B 1/018*     (2006.01)
    *G06F 19/00*     (2011.01)

(56)     References Cited

FOREIGN PATENT DOCUMENTS

| | | |
|---|---|---|
| JP | H06-121579 A | 4/1994 |
| JP | H09-182500 A | 7/1997 |
| JP | 2006-191756 A | 7/2006 |
| JP | 3986344 B2 | 10/2007 |
| JP | 2009-131374 A | 6/2009 |
| JP | 2009-225576 A | 10/2009 |
| JP | 5085684 B2 | 11/2012 |
| WO | 2015/063193 A1 | 5/2015 |

OTHER PUBLICATIONS

Extended Supplementary European Search Report dated Jan. 19, 2018 in European Patent Application No. 15 81 0235.0.

METHOD FOR CONTROLLING MEDICAL MANIPULATOR

FIELD OF THE INVENTION

The present invention relates to a method for controlling a medical manipulator. This application is a continuation application based on PCT Patent Application No. PCT/JP2015/065943, filed Jun. 2, 2015, claiming priority based on Japanese Patent Application No. 2014-127253, filed Jun. 20, 2014, the contents of which are incorporated herein by reference.

DESCRIPTION OF RELATED ART

Heretofore, a medical manipulator that drives a tip end joint and an end effector by transmitting driving force of a plurality of motors via a driving force transmission member such as a wire has been known.

This type of medical manipulator is often used in a patient's body. Examples of this include an endoscope, and a treatment manipulator used by being inserted through a treatment instrument channel of an endoscope.

Therefore, since the insertion part into which the driving force transmission member is inserted is bent in various shapes, driving load varies depending on the operating direction. As a result, even if each motor is driven under similar conditions, the motion of a tip end part may differ from the expected motion in some cases.

As an example of this type of medical manipulator, Patent Document 1 discloses a manipulator system including an endoscope. In the endoscope of this manipulator system, a load amount is calculated by detecting a tension value of the wire which drives a bending piece, and control parameters of a motor are changed according to the bending state which is predicted from this load amount.

For example, the control parameters in Japanese Patent Publication No. 5085684 include "instruction data of observation-treatment slave manipulator, master-slave scale ratio, and sensitivity".

For example, in the manipulator system disclosed in Japanese Patent Publication No. 5085684, motor target angle θ1 which is instruction data is changed to motor target angle θ2 which is obtained by adding a value multiplying a valuable ε indicating the bending state of the endoscope by a constant D to the motor target angle θ1.

SUMMARY OF THE INVENTION

A first aspect of the present invention is a method for controlling method for controlling a medical manipulator which drives a driven part by rotating a motor in accordance with an operation input from an operation part, wherein the method includes: a first step of performing the trial driving when the operation input occurs, evaluating changes in winding resistance based on a temperature rise of the motor, and setting a driving condition of the motor based on the evaluated change in winding resistance; and a second step of performing driving in accordance with the operation input based on the driving condition of the motor set in the first step.

A second aspect of the present invention may be such that in the method for controlling a medical manipulator according to the first aspect, in the first step, a driving condition of the motor may be set by detecting a consumption current, an average applied voltage, and a rotation speed of the motor at the time of the trial driving, and obtaining an evaluation value of winding resistance at in driving from these detection values, measuring a rotation start current at the time of the trial driving and setting a driving current of a value which exceeds a value of the rotation start current, and calculating a PWM signal duty ratio for performing driving based on the evaluation value of the winding resistance and the driving current.

A third aspect of the present invention may be such that in the method for controlling a medical manipulator according to the first aspect or the second aspect, in a case where the medical manipulator is provided with a plurality of the motors, in the first step, a load amount at the time of the trial driving may be evaluated, and a driving start timing may be set for each of the motors such that driving are started from the motor having the highest load amount in descending order in order to reduce variation in driving end timing between the motors, as a driving condition of the motor.

A fourth aspect of the present invention may be such that in the method for controlling a medical manipulator according to the third aspect, in the first step, the load amount may be evaluated from a consumption current at the time of the trial driving.

DETAILED DESCRIPTION OF THE PREFERRED EMBODIMENTS

Hereinafter, an embodiment of the present invention will be described with reference to the accompanying drawings.

First, a medical manipulator system including a medical manipulator controlled by means of the method for controlling a medical manipulator according to the present embodiment will be described.

Figure 1:
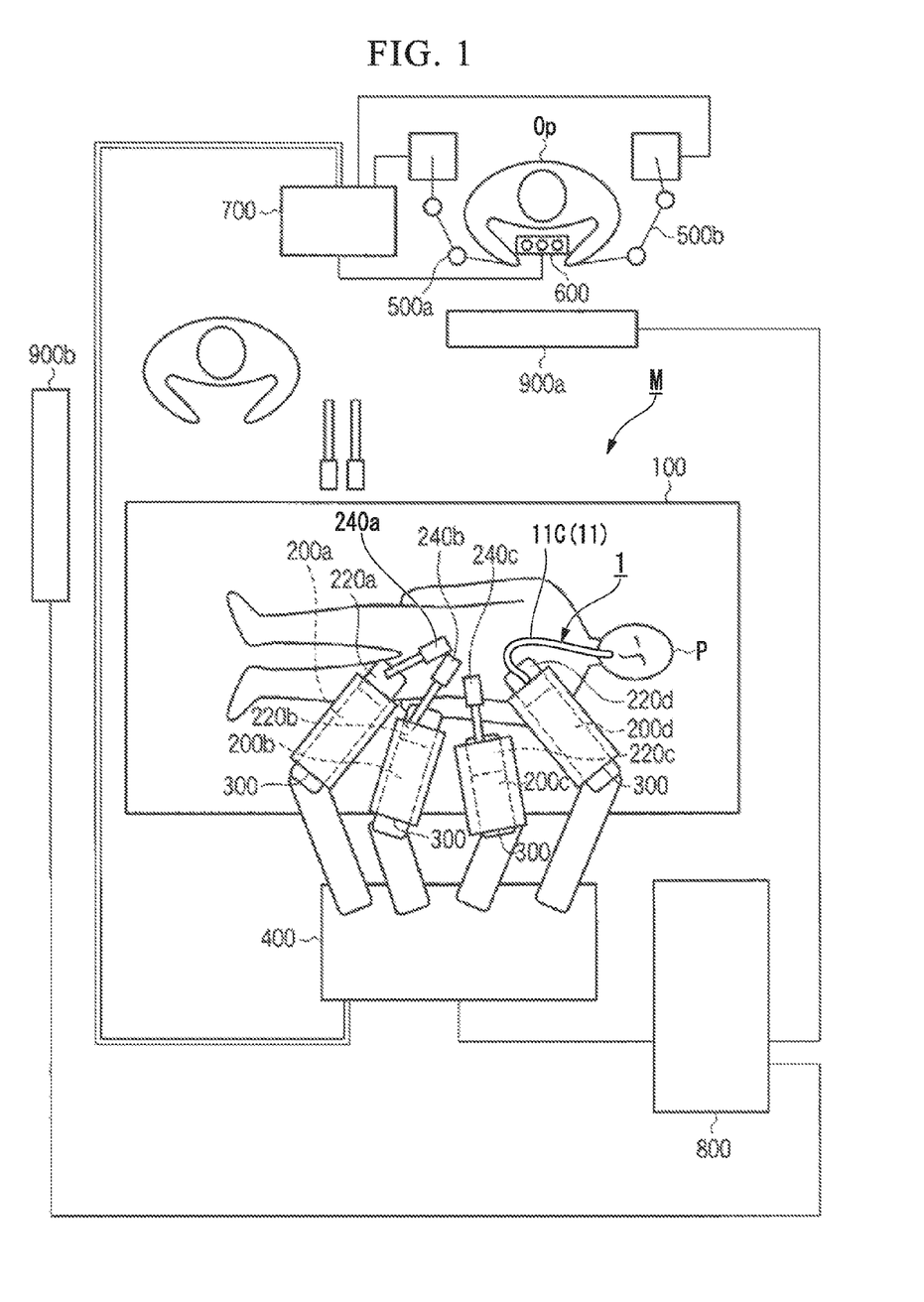
FIG. 1 is a schematic system configuration diagram showing a configuration of a medical manipulator system provided with a medical manipulator controlled by the method for controlling a medical manipulator according to an embodiment of the present invention.

FIG. 1 is a schematic system configuration diagram showing a configuration of the medical manipulator system provided with a medical manipulator controlled by means of the method for controlling a medical manipulator according to the present embodiment.

A medical manipulator 1 controlled by means of the method for controlling a medical manipulator according to the present embodiment is incorporated in a medical manipulator system for performing medical treatment.

First, a configuration of the medical manipulator system in which the medical manipulator 1 is incorporated will be described.

FIG. 1 shows an example of a master-slave type medical manipulator system M. A master-slave type medical manipulator system is a system having two types of arms, namely a master arm and a slave arm and remotely controlling the slave arm so as to follow the operation of the master arm. In the present embodiment, the medical manipulator 1 can be attached to this slave arm.

The medical manipulator system M shown in FIG. 1 has a surgical table 100, slave arms 200a, 200b, 200c, and 200d, a slave control part 400, master arms 500a and 500b (operation parts), an operation part 600, an input processing part 700, an image processing part 800, an operator's display 900a and an assistant's display 900b.

Hereunder, for the sake of simplicity of description, reference signs in alphabetical order "Xa, Xb, ... , Xz" may be expressed as "Xa to Xz" in some cases. For example, "slave arms 200a, 200b, 200c, and 200d" may be expressed as "slave arms 200a to 200d" in some cases.

The surgical table 100 is a table on which an observation-treatment target patient P is placed. In the close vicinity of the surgical table 100, a plurality of slave arms 200a to 200d are disposed in the vicinity of the surgical table 100. The slave arms 200a to 200d may be installed on the surgical table 100.

Each of the slave arms 200a to 200d is configured to have several multi-degree-of-freedom joints. Each of the slave arms 200a to 200d position the medical manipulator 1 and medical manipulators 240a to 240c, which are attached to the distal end side of the slave arms 200a to 200d (the side facing the body cavity of the patient P), with respect to the patient P placed on the surgical table 100 by bending each multi-degree-of-freedom joint. Each multi-degree-of-freedom joint is individually driven by a power unit (not shown in the figure). As the power unit, for example, a motor having a servo mechanism provided with an incremental encoder or a decelerator may be used, and the operation control of the power unit is performed by the slave control part 400.

The medical manipulator 1 and the other medical manipulators 240a to 240c may be rigid or flexible. That is to say, a medical manipulator having an effector for treating on a living body, the effector being configured to be operated by pushing and pulling a rigid rod, or being configured to be operated by pulling a flexible wire, may be appropriately selected as the medical manipulator 1 and the other medical manipulators 240a to 240c. In a case where the medical manipulator 1 and the other medical manipulators 240a to 240c are rigid, a configuration of operating the effector by pulling flexible wire may be provided. In the present embodiment, the medical manipulator 1 has a configuration in which driving power for causing an effector to operate is transmitted to the effector through a flexible wire.

In FIG. 1, for example, the medical manipulators 240a to 240c to be inserted into an abdominal cavity of the patient P are rigid, and for example, the medical manipulator 1 to be introduced from patient's natural orifice such as the mouth into their body via the digestive tract is flexible.

The slave control part 400 includes a CPU and a memory for example. The slave control part 400 stores a predetermined program for performing control of the slave arms 200a to 200d, and controls motion of the slave arms 200a to 200d, or the medical manipulator 1 and the other medical manipulators 240a to 240c based on control signals from the input processing part 700. That is to say, based on the controls signals from the input processing part 700, the slave control part 400 identifies the slave arm (or medical manipulator 1) which is an operation target of the master arm operated by an operator Op, and calculates a driving amount required for causing the identified slave arm to make a movement that corresponds to the master arm operating amount of the operator Op.

The slave control part 400 then controls motion of the slave arm which is the operation target of the master arm in accordance with the calculated driving amount. At this time, the slave control part 400 inputs a driving signal to the corresponding slave arm, and controls a level and polarity of a driving signal such that the driving amount of the slave arm which is the operation target becomes a target driving amount in accordance with a detection signal being input from a position detector of the power unit in accordance with the motion of the corresponding slave arm.

The master arms 500a and 500b are configured with a plurality of link mechanisms. Each link that constitutes the link mechanism has a position detector such as an incremental encoder. The operation amounts of the master arms 500a and 500b are detected in the input processing part 700 by detecting the operation of each link by this position detector.

Examples of the link mechanism of the master arms 500a and 500b include a multiple joint link for operating the position or orientation of the movable part in the medical manipulator 1, and a link performing open-close operations for operating the open-close angle of the grasping motion of a treatment tool.

The medical manipulator system M shown in FIG. 1 is a system operating four slave arms by using two of the master arms 500a and 500b. The medical manipulator system M needs to appropriately switch the slave arm which is the operation target of the master arm. This type of switching is performed, for example, by means of an operation of the operation part 600 performed by the operator Op. Needless to say, this type of switching is not needed if the number of master arms and the number of slave arms are the same and corresponds to the operation target in a one-to-one manner.

The operation part 600 has various types of operation members such as a switching button for switching the slave arms which is the operation target of the master arms 500a and 500b, a scaling change switch for changing the master-slave motion ratio, and a foot switch for performing an emergency stop of the system. In a case where the operator Op operates any one of the operation members that constitute the operation part 600, an operation signal that corresponds to the operation of the corresponding operation member is input to the input processing part 700 from the operation part 600.

The input processing part 700 analyzes the operation signal (operation input) from the master arms 500a and 500b and the operation signal from the operation part 600. The input processing part 700 generates a control signal for controlling the medical manipulator system M according to the result of the operation signal analysis and inputs the control signal to the slave control part 400.

The image processing part 800 performs various types of image processing for displaying the image signal input from the slave control part 400 and generates image data for displaying on the operator's display 900a and the assistant's display 900b. The operator's display 900a and the assistant's display 900b are configured, for example, with a liquid crystal display. The operator's display 900a and the assistant's display 900*b* display an image based on the image data generated in the image processing part 800 according to the image signal acquired via an observation instrument.

In the medical manipulator system M configured in the manner described above, when the operator Op operates the master arms 500*a* and 500*b*, the corresponding slave arms, and the medical manipulator 1 and the other medical manipulators 240*a* to 240*c* attached to this slave arms act so as to correspond to the movement of the master arms 500*a* and 500*b*. As a result, a desired procedure can be performed on the patient P.

In FIG. 1, reference signs 220*a*, 220*b*, 220*c*, and 220*d* denote surgical power transmission adapters. The surgical power transmission adapters 220*a*, 220*b*, and 220*c* respectively connect the slave arms 200*a*, 200*b*, and 200*c* with the rigid medical manipulators 240*a*, 240*b*, and 240*c*. The surgical power transmission adapter 220*d* connects the slave arm 200*d* with the flexible medical manipulator 1.

Moreover, in the present embodiment, a drape 300 configured to partition an area (a clean area) in which sterilization processing is performed and an area (an unclean area) in which sterilization processing is not performed is installed to the medical manipulator system M.

Next, the medical manipulator 1 is described.

Figure 2:
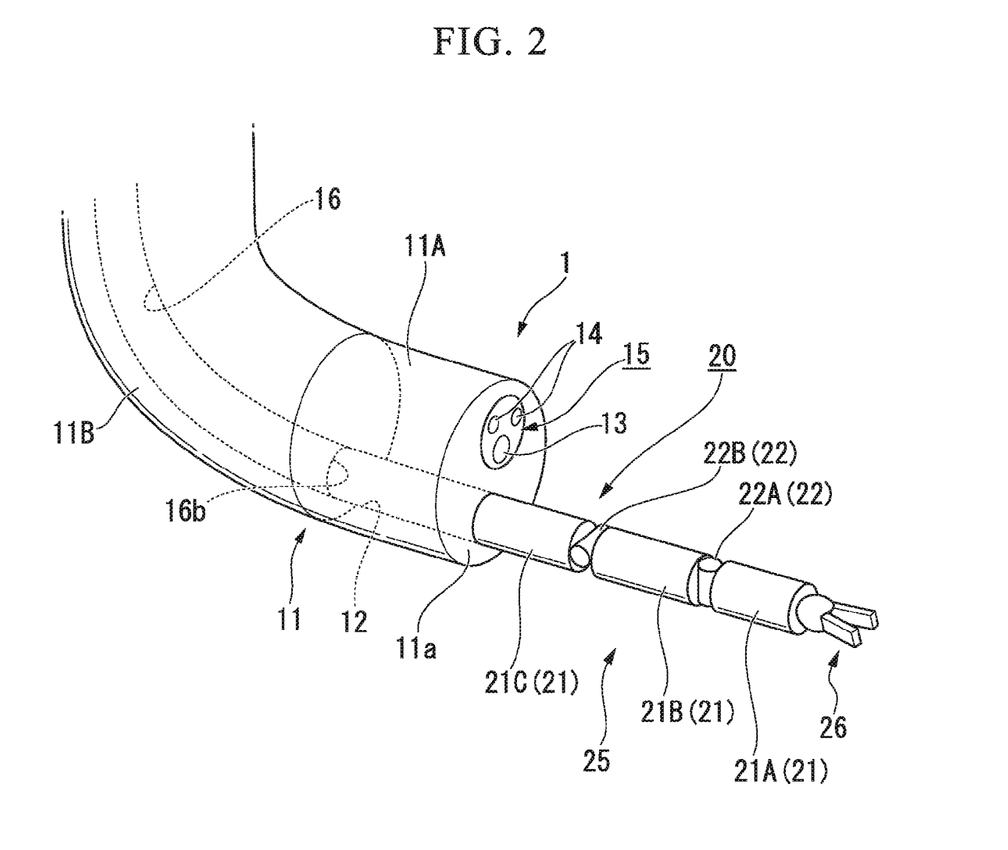
FIG. 2 is a schematic perspective view showing an appearance of a tip end part of the medical manipulator controlled by the method for controlling a medical manipulator according to the embodiment of the present invention.
Figure 3:
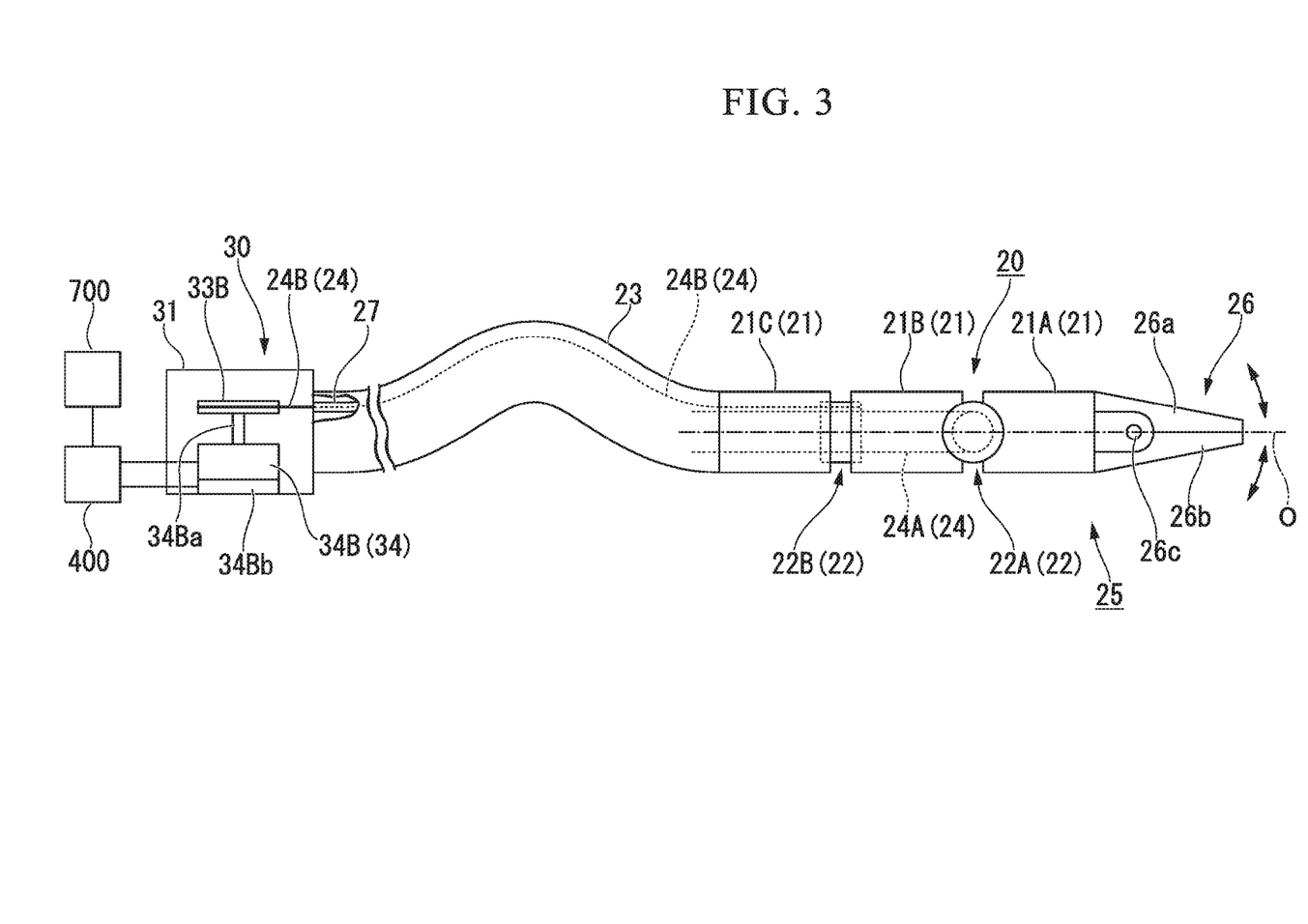
FIG. 3 is a schematic configuration diagram of a principal part of the medical manipulator controlled by the method for controlling a medical manipulator according to the embodiment of the present invention and the medical manipulator system.
Figure 4:
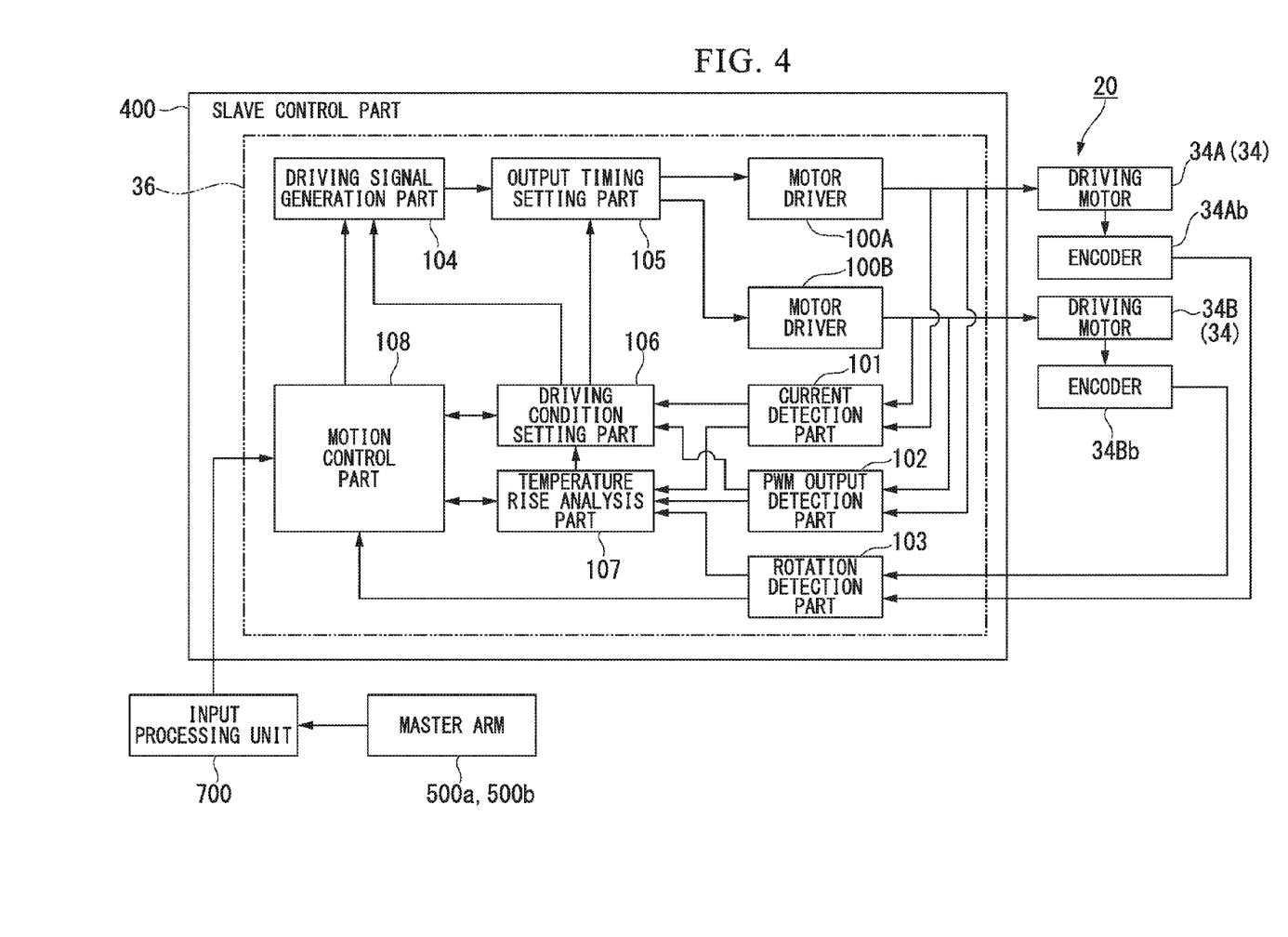
FIG. 4 is a function block diagram showing a function configuration of a principal part of a slave control part that performs the method for controlling a medical manipulator according to the embodiment of the present invention.

FIG. 2 is a schematic perspective view showing an appearance of a tip end part of the medical manipulator controlled by the method for controlling a medical manipulator according to the embodiment of the present invention. FIG. 3 is a schematic configuration diagram, of a principal part of the medical manipulator controlled by the method for controlling a medical manipulator according to the embodiment of the present invention and the medical manipulator system. FIG. 4 is a function block diagram showing a function configuration of the principal part of the slave control part that performs the method for controlling a medical manipulator according to the embodiment of the present invention.

Unless otherwise stated, the description below assumes that in the state where the medical manipulator 1 is incorporated in the medical manipulator system M, the side facing the body cavity of the patient P is taken as the distal side of the medical manipulator 1, and in the medical manipulator 1, the side of the portion connected to the medical manipulator system M on the side away from the patient P is taken as the proximal side of the medical manipulator 1.

As shown in FIG. 2, the medical manipulator 1 has an endoscope manipulator 11 (medical manipulator) which is an elongated member to be inserted into the body of the patient P, and a manipulator treatment instrument 20 (medical manipulator) to be inserted into an interior of the endoscope manipulator 11.

The endoscope manipulator 11 is provided with a tube-shaped flexible insertion part 11C (refer to FIG. 1), a commonly known bent part 11B provided, for example, with a joint ring and a bending piece, and a tip end part 11A that is formed of a column-shaped hard material, in this order from the base end toward the tip end.

When the operation part 600 switches the operation target to the bent part 11B, the orientation of the tip end part 11A is capable of changing by bending the bent part 11B in accordance with an operation input to the master arms 500*a* and 500*b*.

As a mechanism to bend the bent part 11B, a common configuration in which, for example, a driving wire inserted into an inner periphery of the joint ring and the bending piece and fixed to the tip end part 11A is inserted into the insertion part 11C, and the driving wire is pulled by a driving motor or the like disposed on the proximal end side may be employed.

The endoscope manipulator 11 itself also serves as a medical manipulator, and the control method of the present embodiment may be applied thereto.

A treatment instrument channel 16, which serves as a passage for feeding a treatment instrument such as the manipulator treatment instrument 20 to the vicinity of the treatment portion, is provided inside the insertion part 11C and the bent part 11B.

Though illustration is omitted, an insertion opening for inserting the manipulator treatment instrument 20 is formed at a base end part of the treatment instrument channel 16 (proximal end side).

The treatment instrument channel 16 is formed with a flexible tube-shaped member having an inner diameter that at least allows the manipulator treatment instrument 20 to be inserted therethrough. As shown in FIG. 2, a tip end part 16*b* of the treatment instrument channel 16 passes through the tip end part 11A in an axial direction and is connected to a base end side of a through hole part 12 which opens to a tip end surface 11*a* of the tip end part 11A.

As shown in FIG. 2, an observation part 15 is a device for observing a treatment target portion, and the observation part 15 is provided with a commonly known imaging mechanism 13 and an illumination mechanism 14.

The imaging mechanism 13 and the illumination mechanism 14 are arranged within the tip end part 11A, and an electrical wiring and an optical fiber (not shown in the figure) are inserted inside the bent part 11B and the insertion part 11C and is connected to an electrical circuit and a light source in the slave control part 400.

The imaging mechanism 13 and the illumination mechanism 14 have an optical opening window respectively on the tip end surface 11*a* of the tip end part 11A. The imaging mechanism 13 and the illumination mechanism 14 can receive external light in front of the tip end part 11A and can output illuminating light anteriorly through this opening window.

The manipulator treatment instrument 20 is an example of a medical manipulator, which is provided with a joint structure part having a plurality of joints to thereby move or drive a tip end effector, and it is formed in an elongated shaft shape as a whole.

As shown in FIG. 3, the manipulator treatment instrument 20 is provided with a joint 22 (driven part), a shaft-shaped part 21 connected to the joint 22, a grasping pail 26 holding a treatment target or the like, a cylinder-shaped part 23 which is a flexible tube-shaped member, and a driving unit 30 supplying driving force to the joint 22 and the grasping part 26.

The grasping part 26 is an end effector of the manipulator treatment instrument 20. The grasping part 26 is attached to a tip end of the shaft-shaped part 21 on the most tip side (distal end side).

The cylinder-shaped part 23 is connected to the shaft-shaped part 21 on the most base-end side (proximal end side).

The joint 22 is not limited in particular configuration, so long as the joint is a bending joint and is configured to be bent by transmitting driving force from the proximal end by using a power transmission member. The degree of freedom of bending, the direction of bending, and the amount of bending of the joint 22 are not limited in particular.

Hereunder, as an example of the joint 22, the joint 22 and a joint 22A in the order from the proximal end side is described. The joint 22B bends in a direction intersecting with an extending direction of the manipulator treatment instrument 20. The joint 22A bends in a direction orthogonal to a bending direction of the joint 22B.

The joints 22A, 22B both have a pulley (not shown in the figure). Driving wires 24A and 24B are wound on the pulley respectively and their each end parts fixed on the pulleys respectively. The driving wires 24A and 24B are driving force transmission members for transmitting driving force to the joints 22A and 22B.

Hereunder, the joints 22A and 22B or the driving wires 24A and 24B may be referred to simply as joints 22 and driving wires 24 in cases when distinction between the joints 22A and 22B, or between the driving wires 24A and 24B are not clearly shown, or when they are used as a collective term.

Moreover, in this specification, for the salve of simplicity of description, also for the names of members and portions that clearly relate to the joints 22A and 22B, or the driving wires 24A and 24B, additional characters A and B are given to each reference sign in a case of clearly specifying their corresponding relationship. These have substantially the same configuration (including the case of having exactly the same configuration) as each other unless otherwise stated. Furthermore, additional characters are omitted when there is no need for making clear distinction, or when they are used as a collective term.

The shaft-shaped part 21 has shaft-shaped parts 21C, 21B connected by the joint 22B, and a shaft-shaped part 21A connected to the shaft-shaped part 21B by the joint 22A.

As a result, the shaft-shaped part 21C is the shaft-shaped part 21 that is on the base-end most side in the manipulator treatment instrument 20, and the end part on the side opposite of the end part connected to the joint 22B is fixed on the tip end of the cylinder-shaped part 23.

The shaft-shaped part 21A is the shaft-shaped part 21 that is on the tip-end-most side in the manipulator treatment instrument 20, and the grasping part 26 is fixed on the tip end, which is the end part on the opposite side of the joint 22A.

The joints 22B, 22A are connected to both end parts of the shaft-shaped part 21B.

Hereunder, this connected body constituted with the shaft-shaped part 21C, the joint 22B, the shaft-shaped part 21B, the joint 22A, the shaft-shaped part 21A and the grasping part 26 is referred to as a tip end bending part 25.

The grasping part 26 has a pair of holding members 26a and 26b for holding a treatment instrument or tissue for example, and a rotation shaft 26c that rotatably supports the holding members 26a and 26b. The holding members 26a and 26b are rotated about the rotation shaft 26c to open or close in accordance with the operation of the master arms 500a and 500b.

The device for transmitting driving force of the grasping part 26 is not particularly limited. For example, the device for transmitting driving force of the grasping part 26 may be employed a device such that a link, which is not shown in the figure and is connected to the holding members 26a and 26b, is driven by means of a driving wire (not shown in the figure). In the present embodiment, as an example, it is driven by a driving wire similar to the driving wire 24.

As shown in FIG. 3, when closed without holding an object to be held, the grasping part 26 is in a size that does not project from the outer shape of the connected shaft-shaped part 21.

With this type of configuration, the tip end bending part 25 is a shaft-shaped body that is capable of being inserted into the treatment instrument channel 16 and the through hole part 12, and is capable of advancing and retracting.

The cylinder-shaped part 23 is formed with a flexible cylindrical member such as a resin tube. Insertion objects such as driving wires 24A and 24B are inserted into the cylinder-shaped part 23.

Between a base end part of the cylinder-shaped part 23 and the vicinity of the tip end pulley, each of the driving wires 24A and 24B is inserted into a sheath 27 of which locations of both end parts are fixed.

Each sheath 27 is formed with a tightly-wound coil having an inner diameter substantially the same as that of each driving wire 24. Accordingly, length of each sheath 27 is configured almost not to vary even if each of the sheaths 27 is bent in accordance with applying forces.

Although not shown the figure, as examples of objects to be inserted in the cylinder-shaped part 23 other than the driving wire 24, for example, an operation wire for driving the grasping part 26, and electrical wires and optical fibers connected to the observation part 15 are included.

The driving unit 30 is a device portion that drives the driving wire 24 to supply driving force to the joint 22, and drives a driving wire (not shown in the figure) to supply driving force to the grasping part 26.

The driving unit 30 has a plurality of driving motors (motors) 34 inside a base end part casing 31 which is provided at a base end part of the cylinder-shaped part 23. The plurality of driving motors 34 is provided at each driving wire 24 for driving the joint 22. That is to say, although FIG. 3 shows only a driving motor 34B as the driving motor 34, in the present embodiment, the driving motor 34 has driving motors 34A and 34B for driving the driving wires 24A and 24B respectively, as shown in FIG. 4.

Moreover, although it is not specially shown in the figure, the driving unit 30 is arranged at an appropriate position within the slave arm 200d.

As shown in FIG. 3, an output shaft 34Ba of the driving motor 34B is connected to a driving pulley 33B in which the driving wire 24B is wound. As the driving motor 34B is driven to rotate, the driving pulley 33B rotates to allow the driving wire 24B to be pulled in the rotation direction.

The driving motor 34B is configured with a DC motor, and has an encoder 34Bb detecting a rotation position of the output shaft 34Ba.

While the description of the driving motor 34B that drives the driving wire 24B, and related members has been made with reference to FIG. 3, a similar description may be applied to a driving motor 34A, an output shaft 34Aa, a driving pulley 33A, and an encoder 34Ab (refer to FIG. 4), which are not shown in FIG. 3.

In the medical manipulator 1 of this type of configuration, operations of respective device portions are controlled by several control units provided within the slave control part 400. These control units perform a common control method in relation to motor control.

Accordingly, hereunder, as an example, a configuration of a control unit 36 that controls an operation of each driving motor 34 is described, with reference to FIG. 4.

As shown in FIG. 4, the control unit 36 is provided with a motor drivers 100A and 100B, a current detection part 101, a PWM output detection part 102, a rotation detection part 103, a driving signal generation part 104, an output timing setting part 105, a driving condition setting part 106, a temperature rise analysis part 107, and an operation control part 108.

The control operation of the control unit 36 differs between the case of performing the trial driving of each driving motor 34, and the case of performing the full driving. Here, the full driving refers to a driving operation performed for driving each driving motor 34 based on the operation signal from the input processing part 700. The trial driving refers to a driving operation performed prior to the full driving, with a purpose of information acquisition for setting a driving condition in the full driving, which is described later.

While the full driving is performed so that each driving motor 34 rotates toward a target value, the trial driving is performed for a short period of time during which information for setting a driving condition is acquired, and each driving motor 34 either makes no rotation at all or makes a slight amount of rotation even if it rotates.

The motor driver 100A (100B) rotates the driving motor 34A (34B) based on driving signals applied via the output timing setting part 105.

Examples of driving signals applied to the motor driver 100A (100B) include a rotation direction control signal that specifies the rotation direction, a PWM signal that has been pulse-width-modulated to control rotation speed, and a brake signal to brake the rotation.

The current detection part 101 detects each current value supplied from the motor drivers 100A and 100B to the driving motors 34A and 34B, in order to detect consumption current of the driving motors 34A and 34B.

The information of the current values detected by the current detection part 101 is sent to the driving condition setting part 106 and the temperature rise analysis part 107 to be used for calculation performed by each of these parts.

The PWM output detection part 102 monitors PWM signals output from the motor drivers 100A and 100B to the driving motors 34A and 34B, and detects a duly ratio of the output PWM signal, and an average applied voltage for the PWM signal.

The information of the duty ratio detected by the PWM output detection part 102 is sent to the driving condition setting part 106, and is used for calculating a PWM output correction value when performing the trial driving described later.

The information of the average applied voltage detected by the PWM output detection part 102 is sent to the temperature rise analysis part 107, and is used for temperature rise analysis performed by the temperature rise analysis part 107 when performing the trial driving described later.

The rotation detection part 103 acquires output of the encoders 34Ab and 34Bb in the driving motors 34A and 34B, and detects a rotation position and a rotation speed of each driving motor 34.

The information of the rotation position detected by the rotation detection part 103 is used for rotation control of the operation control part 108.

The information of the rotation speed detected by the rotation detection part 103 is sent to the temperature rise analysis part 107, and is used for temperature rise analysis performed by the temperature rise analysis part 107.

The driving signal generation part 104 generates driving signals for performing operation control of each driving motor 34 in accordance with the control information sent from the operation control part 108 and the driving condition setting part 106.

The output timing setting part 105 independently sets timings for outputting driving signals generated by the driving signal generation part 104 to the motor drivers 100A and 100B in accordance with the control information sent from the driving condition setting part 106.

The driving condition setting part 106 sets a driving condition of the driving motors 34A and 34B for the trial driving and the full driving, based on the information sent from the operation control part 108.

Before performing the trial driving, the driving condition setting part 106 sets a driving condition of the trial driving based on operation command value information from the operation control part 108.

Moreover, at the time of performing the trial driving immediately before performing the full driving, the driving condition setting part 106 sets a driving condition of the driving motors 34A and 34B in the full driving based on the operation command value, based on information corresponding to temperature rise acquired from the temperature rise analysis part 107 and current change related information from the current detection part 101.

As a driving condition, the driving condition setting part 106 sets a PWM signal duty ratio for the driving signal generation part 104, and sets an output timing for outputting PWM signals generated in the driving signal generation part 104 to the motor drivers 100A and 100B, for the output timing setting part 105.

The driving condition setting part 106 is connected so as to be able to communicate with the operation control part 108, and operates based on control signals from the operation control part 108.

The specific method of setting driving conditions are explained in the operation description later.

At the time of the trial driving described later, the temperature rise analysis part 107 acquires information of consumption current, average applied voltage, and rotation speed for each of the driving motors 34A and 34B from the current detection part 101, the PWM output detection part 102, and the rotation detection part 103. The temperature rise analysis part 107 then evaluates changes in the winding resistance based on the temperature rise of each of the driving motors 34A and 34B, and sends these evaluation values to the driving condition setting part 106.

The temperature rise analysis part 107 is connected so as to be able to communicate with the operation control part 108, and operates based on control signals from the operation control part 108.

The method of evaluating changes in the winding resistance is explained in the operation description later.

The operation control part 108 monitors operation signals from the input processing part 700 at a constant frequency. If an operation signal is sent, the operation control part 108 analyzes the operation signal and calculates an operation amount required for each of the driving motors 34A and 34B.

Then, in order to realize this operation amount, the operation control part 108 generates each operation command value while performing feedback of the information of a rotation position of each driving motor 34 sent from the rotation detection part 103.

This operation command value is sent to the driving condition setting part 106 and the temperature rise analysis part 107 to be used for setting driving conditions, and is sent to the driving signal generation part 104, and then, a driving signal based on the operation command value is generated by the driving signal generation part 104.

However, upon receiving an operation signal from the input processing part 700, the operation control part 108 exceeds the trial driving during a predetermined period of time before performing operation control of the full driving based on this control signal in order to acquire information for setting a driving condition for the time of the full driving. Therefore, the trial driving is executed during a predetermined period of time.

Details of the control operation performed by the operation control part 108 are explained in the operation described later.

The device configuration of this type of control unit 36, in the present embodiment, consists of a combination of appropriate hardware, and a computer including a CPU, a memory, an input/output interface, and an external memory device and so on. The control function of each function configuration above is realized by means of a control program executed by the hardware or the computer.

Next, the operation of the manipulator treatment instrument 20 in the medical manipulator system M is described, with a primary focus on the medical manipulator control method according to the present embodiment.

Figure 5:
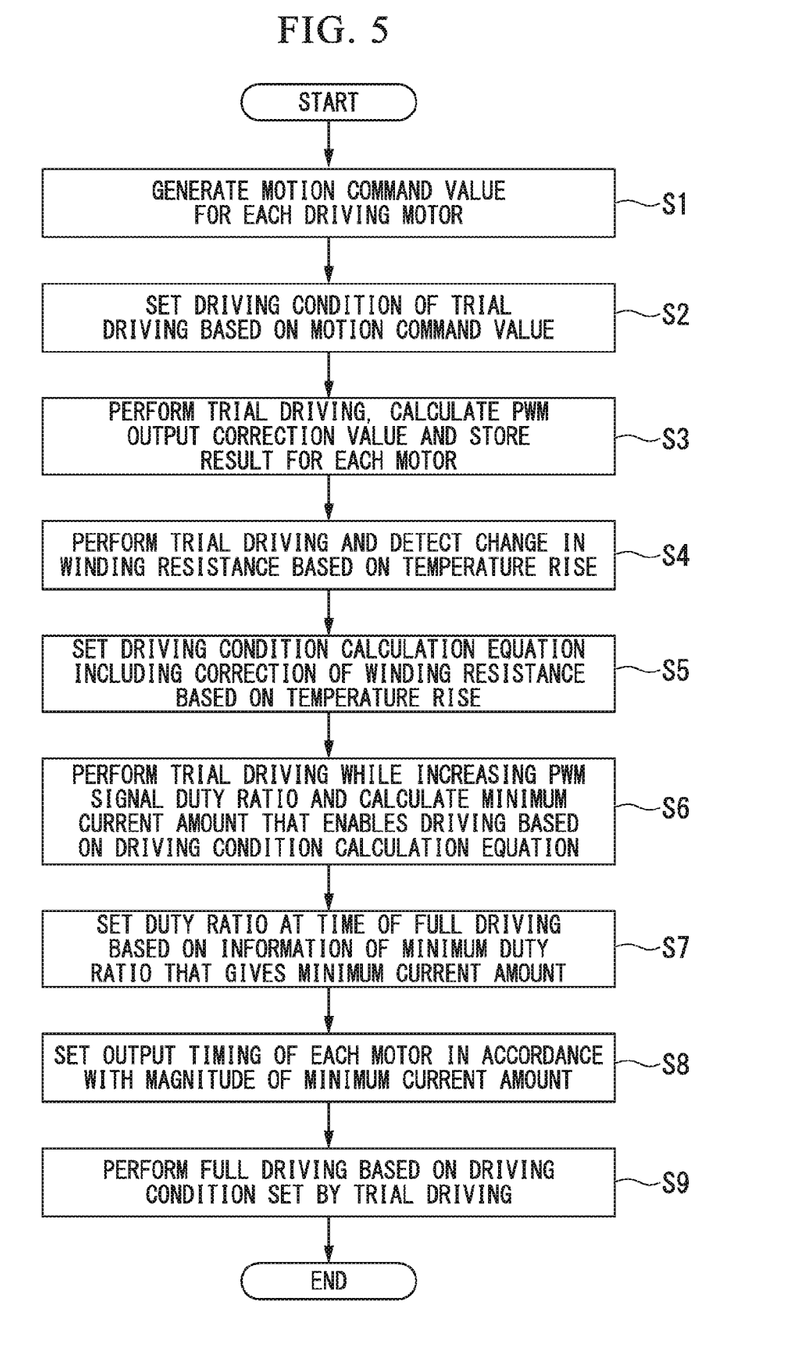
FIG. 5 is a flowchart showing a flow of the method for controlling a medical manipulator according to the embodiment of the present invention.
Figure 6:
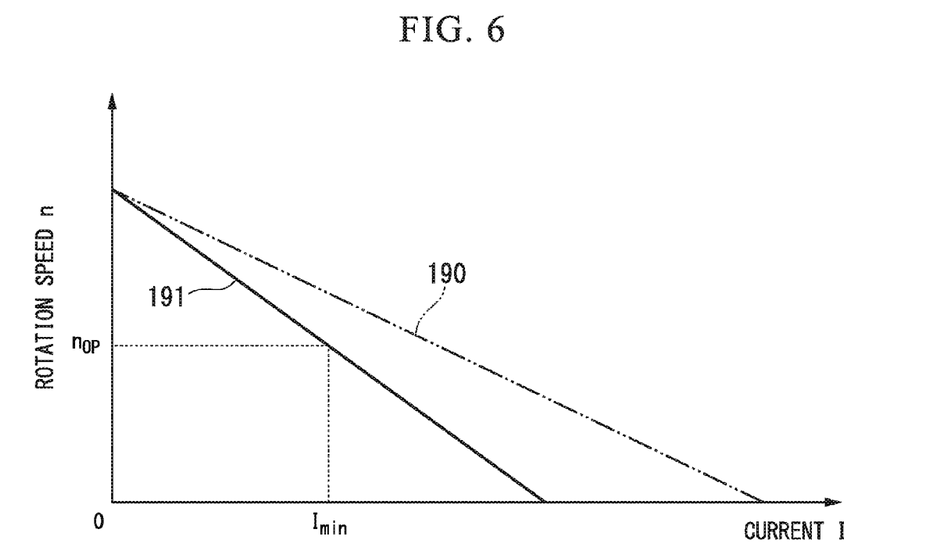
FIG. 6 is a schematic graph showing an example of a driving condition calculation equation in the method for controlling a medical manipulator according to the embodiment of the present invention.

FIG. 5 is a flowchart showing a flow of the method for controlling a medical manipulator according to the present embodiment. FIG. 6 is a schematic graph showing an example of a driving condition calculation equation in the method for controlling a medical manipulator according to the present embodiment. The vertical axis of FIG. 6 represents rotation speed n, and the horizontal axis represents current I. The method for controlling a medical manipulator according to the present embodiment is such that the driven part is driven by rotating a motor, according to an operation input from the operation part.

In order to perform a treatment in the medical manipulator system M by using of the manipulator treatment instrument 20, first, by using of the endoscope manipulator 11, the tip end portion of the manipulator treatment instrument 20 is inserted into the treatment target portion of the body of patient P, and is advanced to the vicinity of the treatment target portion.

Next, as shown in FIG. 2, the tip end bending part 25 of the manipulator treatment instrument 20 is advanced to the forward of the tip end part 11A and then origin determination of the tip end bending part 25 is performed.

As a result, the manipulator treatment instrument 20 is brought to a state of being able to be operated. The operator Op operates the master arms 500a and 500b to perform required procedures while monitoring the image of the treatment target and the tip end bending part 25 which is captured by the imaging mechanism 13 and is displayed on the operator's display 900a.

In general, since the endoscope manipulator 11 is bent depending on the insertion path within patient's body, the treatment instrument channel 16 within the endoscope manipulator 11 is also bent.

Accordingly, the cylinder-shaped part 23 of the manipulator treatment instrument 20, which is inserted into the treatment instrument channel 16, is also bent in the manner similar to the treatment instrument channel 16. As a result, each sheath 27 in the cylinder-shaped part 23 is also bent in various shapes, and a driving load occurs on the driving wire inserted in each sheath 27 depending on the shape of bend. Due to this type of driving load, delays in operation or variation in operation amount may occur in the manipulator treatment instrument 20.

In a medical manipulator, if there are delays in operation or variation in operation amount, correct timing of a procedure may be lost and/or unpredictable movements may occur, preventing smooth execution of the procedure.

This type of driving load can be corrected on some level by which, for example, the actual load in the power transmission system is detected by measuring the tension of the driving wire, and the operation command value is changed according to the load amount.

However, the influence of the magnitude of the load amount on individual driving motors differs depending on individual differences in the motor characteristic of the driving motors and/or heat generation of the driving motor when it is operating. Therefore, the level of operability may not improve in some cases even if the operation command value is corrected regardless of the driving motor.

In the method for controlling a medical manipulator according to the present embodiment, before performing the full driving of the driving motors 34A and 34B based on the operation command value, the load amount is evaluated by performing the trial driving, and an appropriate driving condition with respect to the load amount is set, and then the full driving is performed.

The control method of the present embodiment is a method in which Step S1 to Step S9 are executed according to the flow illustrated in FIG. 5 every time when an operation signal for performing driving is received from the input processing part 700.

In the medical manipulator 1, the input processing part 700 monitors operation inputs of the operation part 600 and the master arms 500a and 500b, at a constant frequency, for example, every 1 ms.

When the input processing part 700 analyzes that the detected operation input is an operation input for driving the tip end bending part 25 of the manipulator treatment instrument 20, the input processing part 700 sends an operation signal to the operation control part 108 of the manipulator treatment instrument 20.

Step S1 is a step of generating an operation command value for each driving motor.

When the operator Op operates the master arms 500a and 500b after having switched the operation target to the manipulator treatment instrument 20 of the slave arm 200d by means of the operation part 600, the input processing part 700 analyzes the operation signals of the operation part 600 and the master arms 500a and 500b.

The operation signal analyzed by the input processing part 700 is sent to the operation control part 108 of the control unit 36, as information of an operation to be performed by the manipulator treatment instrument 20. For example, the information including a position to which the grasping part 26 of the manipulator treatment instrument 20 needs to move and a posture after the movement is sent.

The operation control part 108 calculates the driving amount for the joints 22A and 22B in the tip end bending part 25 required to realize these position and posture of the grasping part 26, and generates an operation command value that expresses the rotation direction, rotation amount, and rotation speed of the driving motors 34A and 34B for realizing this driving amount.

This completes Step S1.

Next, Step S2 is performed. This step is a step of setting a driving condition of the trial driving based on the operation command value.

There are mainly three purposes for the trial driving in the present embodiment.

The first purpose is to calculate a PWM output correction value for correcting errors in the PWM signal duly ratio output to each driving motor 34.

The second purpose is to be able to perform correction by calculating winding resistance based on temperature rise in each driving motor 34.

The third purpose is to evaluate the minimum current amount required in performing the full driving.

For any one of these purposes, the rotation direction is matched with the rotation direction of the operation command value.

Trial driving performed for the first and second purposes (hereunder, referred to as first trial driving) is performed only for a predetermined certain period of time, where the duty ratio is fixed to the default duty ratio corresponding to the rotation speed of the operation command value. Here, as the certain period of time, there is set a shortest possible period of time within a range where data can be acquired in Step S3 and Step S4 described later. For example, it is set to approximately 20 μs.

The trial driving performed for the third purpose (hereunder, referred to as second trial driving) is such that since driving is performed while gradually increasing the duty ratio from 0%, there is set a length of time consumed when increasing the duty ratio from 0% to 100%. This time setting can be performed regardless of the operation command value, and, for example, it is set to approximately 200 μs.

In any of these trial drivings, the timing of outputting a driving signal is a timing of outputting signal to the motor drivers 100A and 100B immediately after a driving condition has been set for the driving signal generation part 104 without providing temporal difference in particular.

When the control signal for setting the driving condition of the trial driving and the operation command value are sent from the operation control part 108 to the driving condition setting part 106, the driving condition setting part 106 sets the driving condition described above, and sets it in the driving signal generation part 104 and the output timing setting part 105.

This completes Step S2.

Next, Step S3 is performed. This step is a step of performing the first trial driving, calculating a PWM output correction value for each driving motor 34, and storing the value for each driving motor 34.

When Step S2 ends, the operation control part 108 sends a control signal for starting a generation of a driving signal to the driving signal generation part 104. As a result, the driving signal generation part 104 generates a PWM signal, based on the driving condition set by the driving condition setting part 106. This PWM signal is output to the motor drivers 100A and 100B at the timing set by the output timing setting part 105. Thereby, the first trial driving of the driving motors 34A and 34B is started.

The PWM signals output from the motor drivers 100A and 100B to the driving motors 34A and 34B are monitored by the PWM output detection part 102. The PWM output detection part 102 sends the output duty ratio information to the driving condition setting part 106.

The driving condition setting part 106 calculates ΔD=Dout−D0 which is a difference between the output PWM signal duty ratio D0 and the duty ratio Dout sent from the PWM output detection part 102 for each of the driving motors 34A and 34B, and stores them as PWM output correction values $\Delta D_A$ and $\Delta D_B$ respectively.

This type of change in duty ratio occurs due to a hardware-unique reason such as signal transmission delay in a switching component or the like. Therefore, in general, ΔD takes a positive value, and the duty ratio becomes excessively large in comparison with the operation command value.

Hence, the PWM output correction values $\Delta D_A$ and $\Delta D_B$ are used for correcting the duty ratio calculated from the operation command value in the full driving.

As a result, hardware-unique PWM signal changes are corrected, and therefore, the driving motors 34A and 34B are possible to perform driving more faithfully to the operation command value. Moreover, heat generation due to a rise in average applied voltage caused by an increase in the duty ratio is also capable of being suppressed.

This completes Step S3.

If the value of ΔD is too high, there is a possibility that abnormality is occurring in the hardware. Therefore, an appropriate threshold value is preliminarily provided. If the threshold value is exceeded, it is possible to determine malfunction, display a warning message on the operator's display 900a and the assistant's display 900b, and stop the operation of the manipulator treatment instrument 20.

Furthermore, the driving condition setting part 106, also in performing the full driving described later, monitors Dout−D0, and if Dout−D0 exceeds a predetermined allowed value, the driving condition setting part 106 determines malfunction, and display a warning message on the operator's display 900a and the assistant's display 900b, thereby the operation of the manipulator treatment instrument 20 is capable of being stopped.

Next, Step S4 is performed. This step is a step of performing the first trial driving, and detecting changes in the winding resistance based on temperature rise in each driving motor 34.

This step can be performed at an appropriate timing at which the first trial driving has started and at which temperature rise due to the first trial driving can be measured. Therefore, performing this step after Step S3 is merely an example, and this step is not imperative to perform after Step S3. For example, this step may be performed prior to Step S3, or may be performed in parallel with Step S3.

In a DC motor, rotation speed n is expressed as Equation (1) below. Therefore, where the horizontal axis represents current I, and the vertical axis represents rotation speed n as shown in FIG. 6, the relationship between current I and rotation speed n under a condition where winding resistance R and average applied voltage DUTY are constant is expressed as a linear line.

$$n = k_n \cdot (\text{DUTY} - R \cdot I) \quad (1)$$

Here, the constant of proportion $k_n$ takes a value unique to each motor. For example, the constant of proportions of the driving motors 34A and 34B are $k_{nA}$ and $k_{nB}$ respectively.

Winding resistance R is, for example, expressed as Equation (2) below, as a function R (T) of temperature T.

$$R(T) = R_{25} \cdot \{1 + \alpha \cdot (T - T_{25})\} \quad (2)$$

Here, $R_{25}$ is the winding resistance of the motor where temperature $T_{25}=25(° C.)$, and α is a linear expansion coefficient of the wire material.

For example, when expressing Equation (1) with the linear line 190 in FIG. 6 where temperature is 25° C., Equation (1) in a case where the temperature becomes T (where $T>T_{25}$) due to temperature rise in the motor, is expressed as the linear line 190 in FIG. 6 because the winding resistance becomes R (T) (where R (T)>$R_{25}$).

That is to say, if the driving condition does not change, then as the temperature rises, rotation speed n decreases. Therefore, the driving motor 34 performs a lower speed compared to the rotation speed of the operation command value, and therefore, the response time of the driving motor 34 is reduced. Moreover, if temperature rises differently for each driving motor 34, the amount of reduction in response time differs. Therefore, response time of each driving motor 34 varies, and as a result, concerted operation of each joint 22 is disturbed.

This type of reduction and variation in response time of the joint 22 would compromise the level of operability of the manipulator treatment instrument 20, and has a possibility of causing interruption of surgical procedures.

Consequently, in the present embodiment, driving condition of the full driving is changed in accordance with changes in winding resistance based on temperature rise.

Therefore, in this step, based on Equation (3) below, the temperature rise analysis part 107 evaluates changes in winding resistance based on temperature rise for each of the driving motors 34A and 34B, and calculates winding resistance $R_T$ for each of the driving motors 34A and 34B.

$$R_T = \{DUTY_T - (n_T/k_n)\}/I_T \quad (3)$$

Here, $DUTY_T$ is an average applied voltage at the time of the first trial driving, which has been sent from the PWM output detection part 102. $n_T$ is a rotation speed at the time of the first trial driving, which has been sent from the rotation detection part 103. $I_T$ is a consumption current at the time of the first trial driving, which has been sent from the current detection part 101.

The winding resistance $R_T$ calculated by the temperature rise analysis part 107 is sent, as winding resistances $R_{TA}$ and $R_{TB}$ (winding resistance evaluation values) for each of the driving motors 34A and 34B, respectively to the driving condition setting part 106 and stored in the driving condition setting part 106.

This completes Step S4.

Next, Step S5 is performed. This step is a step of setting a driving condition calculation equation that includes correction for winding resistance due to temperature rise.

The driving condition setting part 106 uses $R_T$ sent from the temperature rise analysis part 107, and sets Equation (4) below as a driving condition calculation equation.

$$n = k_n \cdot (DUTY - R_T \cdot I) \quad (4)$$

The Equation (4) above may be set as an equation or a data table, as long as the Equation (4) is set in a format which is capable of calculating unknowns based on variables given by the driving condition setting part 106.

Hereunder, an example is described where Equation (4) above is stored as an equation for calculating unknowns.

Once setting of the driving condition calculation equation is completed, the first trial driving ends.

This completes Step S5.

Next, Step S6 is performed. This step is a step of performing the second trial driving while increasing the PWM signal duty ratio, and setting a minimum current value that enables driving, based on the driving condition calculation equation.

The operation control part 108 sends a control signal for starting the second trial driving to the driving condition setting part 106.

In the driving condition setting part 106, a driving condition for driving each driving motor 34 is set such that the PWM signal duty ratio is gradually increased from 0%.

After completing the set of the driving condition, the operation control part 108 sends a control signal for starting driving signal generation to the driving signal generation part 104. As a result, the driving signal generation part 104 generates a driving signal such as a PWM signal, based on the driving condition set by the driving condition setting part 106. This driving signal is output to the motor drivers 100A and 100B at the timing set by the output timing setting part 105. Thereby, the second trial driving of the driving motors 34A and 34B is started.

When the second trial driving has started and the duty ratio is increased and electric power exceeding the load amount of each driving motor 34 is supplied, each driving motor 34 starts to rotate.

The driving condition setting part 106 detects the start of rotation of each driving motor 34 by monitoring the current amount sent from the current detection part 101.

For this reason, the driving condition setting part 106 stores a predetermined threshold value of current amount change for detecting that each of the driving motor 34 starts rotation based on changes in the current amount.

The current amount decreases due to inertia when rotation of the driving motor 34 is started. Therefore, the driving condition setting part 106 is possible to detect rotation start by monitoring the change ratio of current.

In a case where the magnitude of current amount change ratio becomes greater than or equal to the threshold value, the driving condition setting part 106 notifies the operation control part 108, determines the maximum value of the current amount, which has been monitored up until this point in time, as the rotation start current, calculate the current amount such that this rotation start current is multiplied by a predetermined coefficient, as the minimum current amount $I_{min}$ (driving current). As the predetermined coefficient, an appropriate coefficient 1 or greater is set preliminarily, while taking a margin for measurement errors into consideration.

The operation control part 108, which has been notified of the rotation start of the driving motor 34 by the driving condition setting part 106, sends a control signal for stopping the second trial driving to the driving signal generation part 104.

In this manner, the second trial driving is completed, and the minimum current amount $I_{min}$ is calculated as the minimum current amounts $I_{minA}$ and $I_{minB}$ for each driving motor 34.

This completes Step S6.

Next, Step S7 is performed. This step is a step of setting a duty ratio $D_{OP}$ in the full driving based on the information of the minimum duty ratio $D_{min}$ giving the minimum current amount $I_{min}$ calculated in Step S6.

Specifically, the driving condition setting part 106 calculates a duty ratio $D_{OP}$ in the full driving based on Equation (5) below, and the duty ratio $D_{OP}$ of the driving signal generation part 104 is set.

$$D_{OP} = \{(n_{OP}/k_n) - R_T \cdot I_{min}\}/E - \Delta D \quad (5)$$

Here, "$n_{OP}$" is a rotation speed in an operation command value of the full driving. "E" represents voltage for generating a PWM signal.

As a driving condition, the error in the duty ratio associated with changes in the winding resistance detected in the trial driving and signal delays is corrected by setting a duty ratio $D_{OPA}$ ($D_{OPB}$) that is calculated by substituting $n_{OPA}$ ($n_{OPB}$), $R_{TA}$ ($R_{TB}$), $I_{minA}$ ($I_{minB}$), and $\Delta D_A$ ($\Delta D_B$) respectively for $n_{OP}$, $R_T$, $I_{min}$, and $\Delta D$ of Equation (5) above. Therefore, if a PWM signal occurs, a full driving based on the rotation speeds $n_{OPA}$, $n_{OPB}$ of the operation command value can be started.

This completes Step S7.

Next, Step S8 is performed. This step is a step of setting an output timing of each driving motor 34, according to the magnitude of the minimum current amount $I_{min}$ calculated in Step S6.

The minimum current amounts $I_{minA}$ and $I_{minB}$ calculated in Step S6, which are consumption currents at the time of rotation start of the second trial driving of the driving motors 34A and 34B, represent the load amounts of the driving motors 34A and 34B. When load amounts differ like this, acceleration times taken until a certain rotation speed is reached differ even if rotations start at the same time. Therefore, for this difference, a temporal difference in the length of time until the target driving ends may occur.

In the present embodiment, in order to suppress variation in driving time associated with this type of cause, PWM signal output is started first for the greater one among the minimum current amounts $I_{minA}$ and $I_{minB}$, and is delayed the output timing for the smaller one among the minimum current amounts $I_{minA}$ and $I_{minB}$.

The amount of the delay in output timing is obtained preliminarily by the relationship between the load amount and corresponding to the minimum current value and the acceleration time from experiments and is stored as an experiment equation and/or data table in the driving condition setting part 106.

For example, in a case of $I_{minA} > I_{minB}$, the driving condition setting pail 106 calculates a delay amount $\Delta t$ of the timing of output to the motor driver 100B as $\Delta t = f(I_{minA} - I_{minB})$, based on a preliminarily set function f, and sets $\Delta t$ to the output timing setting part 105.

This completes Step S8.

Next, Step S9 is performed. This step is a step of performing the full driving based on the driving condition set by the first and second trial drivings.

The operation control part 108 sends a control signal to start generating a driving signal to the driving signal generation part 104. As a result, the driving signal generation part 104 generates a driving signal including a PWM signal based on the driving condition of the full driving set by the driving condition setting part 106. This PWM signal is output to the motor drivers 100A and 100B at the full driving output timing set by the output timing setting part 105. Thereby, the full driving of the driving motors 34A and 34B is started.

As a result, the driving motors 34A and 34B rotate based on the operation command value calculated by the operation control part 108, and the joints 22A and 22B of the tip end bending part 25 are driven so as to take positions and orientation based on the operation of the master arms 500a and 500b.

This completes Step S9.

In this manner, the trial driving and the full driving described above are repeatedly performed each time when an operation signal is sent to the operation control part 108.

Steps S1 to S8 above constitute a first step in which, the trial driving is performed when an operation input occurs, changes in winding resistance based on temperature rise in the motor is evaluated, and a driving condition of the motor is set based on the evaluated winding resistance changes.

Step S9 above constitutes a second step of performing driving that corresponds to the operation input based on the driving condition of the motor set in the first step.

The control method for the tip end bending part 25 of the manipulator treatment instrument 20 is described above. However, the grasping part 26 of the manipulator treatment instrument 20 and the bent part 11B of the medical manipulator 1 are also controlled by means of a similar control method.

According to the method for controlling a medical manipulator of the present embodiment, the trial driving is performed to evaluate changes in the winding resistance of the motor based on the temperature rise when an operation input occurs, and a driving condition of the motor is set based on the changes in the evaluated winding resistance. Therefore, the motor is capable of being operated accurately and promptly even if the load amount changes.

That is to say, since the trial driving is performed and changes in winding resistance based on the load amount and temperature rise are evaluated every time when an operation signal is sent, it is possible to operate the motor accurately and promptly even if the load amount changes while executing a procedure.

Moreover, in a case where a plurality of motors are provided, the trial driving is performed for each motor, and changes in winding resistance based on the load amount and temperature rise are evaluated. Therefore, it is possible to operate the motor accurately and promptly even if the load amount changes in each motor, for example, due to the difference in driving direction.

In particular, in the present embodiment, in the first trial driving, a PWM signal output error is detected, a PWM output correction value $\Delta D$ is calculated, and the duty ratio in a driving condition is corrected. As a result, it is possible to correct variations in driving conditions associated with individual differences between hardware such as motors and signal circuits.

In particular, in a case where the driving frequency of the motor is a high frequency such as 500 kHz, a duty ratio error becomes relatively greater by the influence of the error associated with signal output delay.

For example, assume that the duty ratio is 10% and an error of 100 ns associated with a delay in signal output due to the hardware occurs, between the case where the driving frequency is 50 kHz and the case where it is 500 kHz. In this case, the duty ratio error is 50% (=100×100 ns/0.2 μs) with frequency 500 kHz, whereas the duly ratio error is 5% (=100×100 ns/2 μs) with frequency 50 kHz. As a result, while the duty ratio changes from 10% to 15% with 500 kHz, in the present embodiment, it is possible to prevent this type of error from occurring.

In the description of the above embodiment, there has been described an example of the case where a PWM output correction value is calculated in the trial driving. However, for example, in a case where the motor driving frequency is low or in a case where the hardware error is small, it is possible to omit correction using a PWM output correction value.

In the description of the above embodiment, there has been described an example of the case where driving motors 34A and 34B, which are two motors, are provided as motors in the medical manipulator. However, this is merely an example, and the number of motors is not limited to this. For example, the medical manipulator may be provided with three or more motors.

Furthermore, there may be provided a single motor only. However, in this case, Step S8 above is removed.

In the description of the above embodiment, changes in winding resistance are obtained without measuring temperature rises. However, the temperature of the motor may be measured with use of a temperature sensor or the like, and winding resistance $R_T$ may be calculated using Equation (2) above.

While the above is a description of each embodiment of the present invention, the technical scope of the invention is not limited to the above embodiment, and the combination of the constituents in each embodiment may be changed, and removal or various modifications may be made to each constituent, without departing from the scope of the invention.

What is claimed is:

1. A method for controlling a medical manipulator which drives a driven part by rotating a motor in accordance with an operation input from an operation part, wherein the method includes:
 a first step of performing the trial driving when the operation input occurs, evaluating changes in winding resistance based on a temperature rise of the motor, and setting a driving condition of the motor based on the evaluated change in winding resistance; and
 a second step of performing driving which corresponds to the operation input based on the driving condition of the motor set in the first step.

2. The method for controlling a medical manipulator according to claim 1, wherein
 in the first step, a driving condition of the motor sets by detecting a consumption current, an average applied voltage, and a rotation speed of the motor at the time of the trial driving, and obtaining an evaluation value of winding resistance in driving from these detection values,
 measuring a rotation start current at the time of the trial driving and setting a driving current which exceeds the rotation start current, and
 calculating a PWM signal duty ratio for performing driving based on the evaluation value of the winding resistance and the driving current.

3. The method for controlling a medical manipulator according to claim 1, wherein
 in a case where the medical manipulator is provided with a plurality of the motors,
 in the first step,
 a load amount at the time of the trial driving is evaluated, and
 a driving start timing is set for each of the motors such that driving are started from the motor having the highest load amount in descending order in order to reduce variation in driving end timing between the motors, as a driving condition of the motor.

4. The method for controlling a medical manipulator according to claim 3, wherein
 in the first step,
 the load amount is evaluated from a consumption current at the time of the trial driving.

* * * * *